United States Patent [19]

Garnier

[11] 4,381,777
[45] May 3, 1983

[54] SYRINGE WITH OSCILLATING NEEDLE

[75] Inventor: Marcel Garnier, Besancon, France

[73] Assignee: Micro-Mega S.A., Besancon, France

[21] Appl. No.: 225,181

[22] Filed: Jan. 13, 1981

[30] Foreign Application Priority Data

Jan. 14, 1980 [FR] France ............................... 80 00942

[51] Int. Cl.³ ............................................. A61M 5/18
[52] U.S. Cl. .............................. 604/188; 128/DIG. 1
[58] Field of Search .................... 128/218 R, 215, 221,
128/218 N, DIG. 1, 218 A, 92 E; 99/533, 532

[56] References Cited

U.S. PATENT DOCUMENTS 3,811,442  5/1974  Maroth .......................... 128/218 R
4,124,026 11/1978  Berner et al. ...................... 128/92 E Primary Examiner—John D. Yasko
Attorney, Agent, or Firm—Mason, Fenwick & Lawrence

[57] ABSTRACT

Anaesthetic may be injected directly into the bone using a syringe in combination with a mechanism for causing the syringe needle to oscillate about its axis. The mechanism may be driven by a drive unit of the type conventionally used to power dental instruments.

5 Claims, 11 Drawing Figures

SYRINGE WITH OSCILLATING NEEDLE

BACKGROUND OF THE INVENTION

Syringes for administering injections are well known and the various types available on the market are generally quite satisfactory. Further, techniques for using the known syringes are well developed. However, practitioners, specially dental practitioners, encounter certain problems in this regard, sometimes in cases of real necessity, but more and more often as the result of requests made by patients.

It is known that local anaesthetic intended to render insensible a tooth on which the dentist is to operate is more effective when injected directly into porous bone. In the case of the mandible, the porous bone is covered by a hard shell, the osseous cortex, which must be perforated before the needle of the syringe can enter the porous bone.

SUMMARY OF THE INVENTION

An object of the invention is to provide a syringe including a needle capable of penetrating the osseous cortex so as to inject anaesthetic into the porous bone.

This object is achieved by providing the syringe with means for rotating the needle about its axis during the injection process. Although it falls within the scope of the invention for the needle to be rotated continuously in one direction, this action could prove dangerous or at least make necessary special precautions. For this reason, it is preferred to cause the needle to oscillate in an angular sense about its axis, hereby avoiding injury or breakage if the needle bends following deflection.

The invention may be embodied in a purpose-constructed syringe including means for expelling the anaesthetic during the injection operation and means for causing the needle to rotate to oscillate. However, since virtually every dental practitioner has a syringe of the carpule type as described in French Pat. No. 1 583 163 issued to the assignees of the present invention as well as a micromotor for driving his various hand instruments, it is preferred to associate such a syringe with a device for transforming the continuous rotation of the output shaft of the motor into angular oscillations of the needle, such device being interposed between the syringe and the motor. In the event that the syringe is of the type disclosed in the above-mentioned patent, the syringe incorporates a serrated thumb-wheel to enable the injection needle to be rotated manually for the purpose of appropriately positioning the beveled end of the needle relative to the surface to be injected. Conveniently, the device for converting continuous rotation into angular oscillations of the needle about its axis may consist of a crank-pin fast with a pinion drivable directly or indirectly by the output shaft of the motor, the crank-pin being movable in a groove in or associated with means for cooperation with the thumb-wheel. In an alternative embodiment, the crank-pin may cooperate with a pivotal fork used to convert continuous rotation of the output shaft into oscillation of the thumb-wheel.

DESCRIPTION OF THE DRAWINGS

FIG. 3 shows disassembled and partly in section the mechanism for causing the needle of the syringe shown in FIG. 2 to oscillate about its axis.

DESCRIPTION OF PREFERRED EMBODIMENTS

Figure 1:
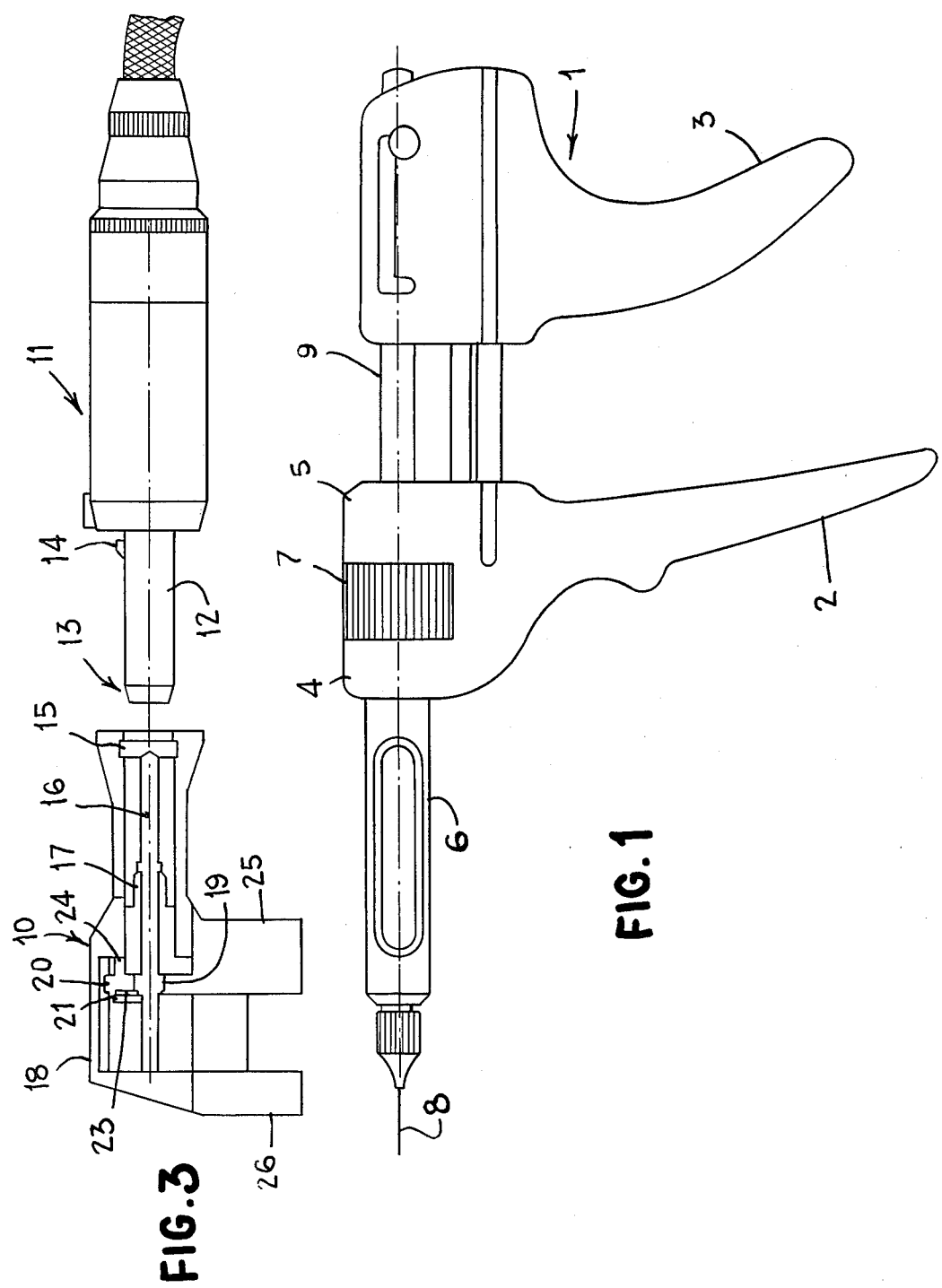
FIG. 1 is a plan view of a pistol syringe of known type.

FIG. 1 shows a syringe of known type adapted to operate with ampoules of the carple type. The syringe comprises a pistol-grip type handle consisting of a portion 2 which remains stationary in operation, and a portion 3 which is advanced towards the stationary portion when the handle is squeezed. The handle portion 2 is integral with a body supporting a sleeve 6 which contains the ampoule when in use. The body is bifurcated, having spaced portions 4 and 5 between which is located a thumb-wheel 7 which may be turned manually to rotate the sleeve 6 and the needle 8 fast with the sleeve, for the purpose of suitably positioning the beveled end of the needle relative to the body of the patient. The handle portion 3 is integral with a body carrying guide rods on which the relatively movable part is guided and a piston 9 extending into the sleeve 6 for the purpose of expelling liquid from the ampoule through the needle 8 as the two parts of the syringe come together.

Figure 2:
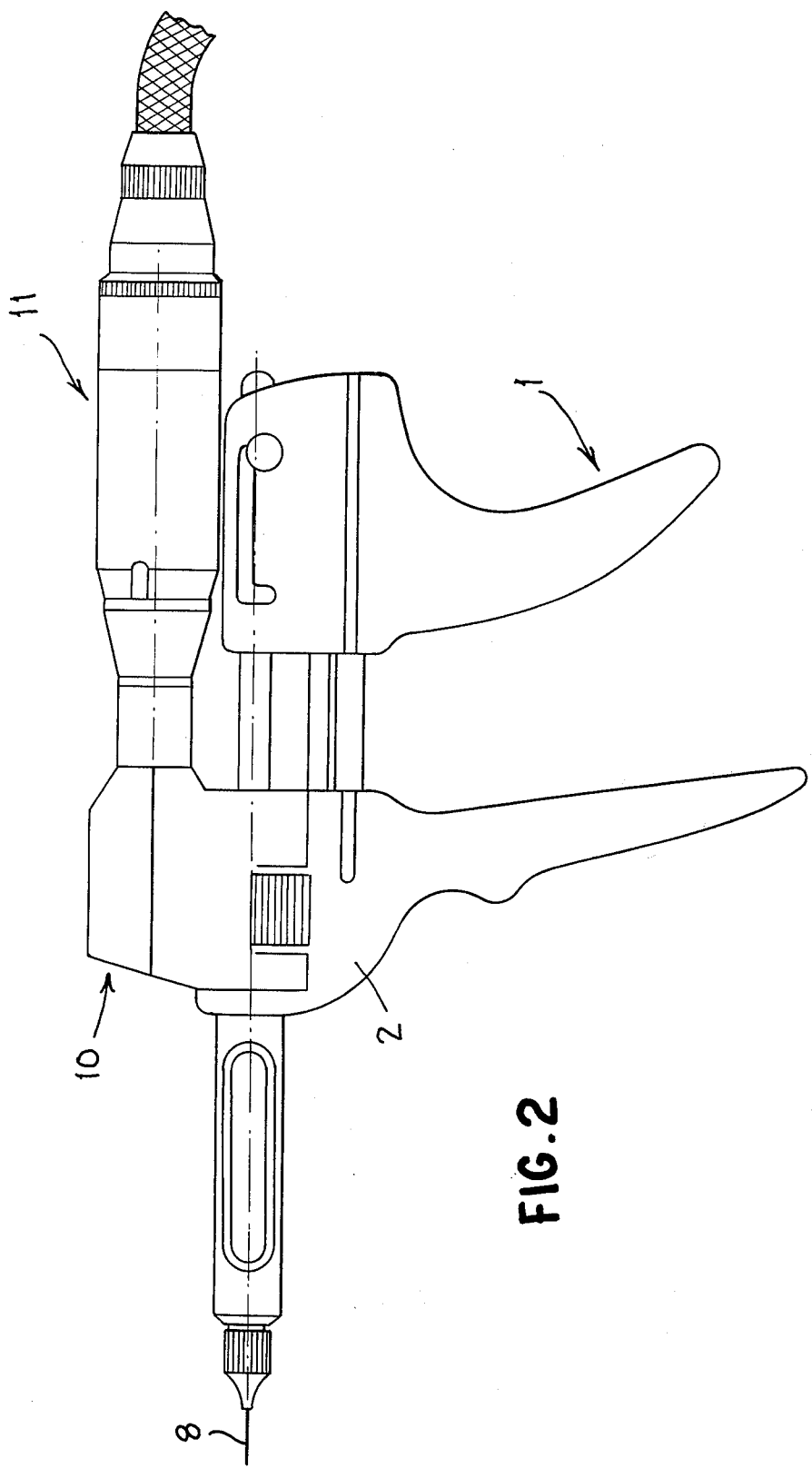
FIG. 2 is a plan view of a syringe of the type shown in FIG. 1, adapted in accordance with the invention.

This known syringe is modified to carry out the invention as shown in FIG. 2 by coupling the syringe through the intermediary of a transmission device 10, to a drive unit 11 of the type used to power other hand instruments used in dentistry, for example drills, buffing wheels and the like. The drive unit 11 has a head which houses a micro-motor which may be of the pneumatic or electric type. As shown in FIG. 3, a sleeve 12 projects from the head and houses the output shaft (not shown) of the motor. The sleeve is provided with a leaf spring 13 and ratchet 14 to enable the sleeve to be retained within a suitably adapted throat 15 of an adaptor. This arrangement is described in more detail in German Pat. No. 1 303 676 in the name of the assignees of the present invention. The adaptor forms part of the housing 18 of the transmission device 10, the housing being adapted to straddle the body portions 4 and 5 of the syringe as shown in FIG. 2. The housing includes tabs 25 and 26 spaced axially of the device and adapted to be locked to the body portions 4 and 5, for example by a ratchet mechanism in such a way as to leave the thumb-wheel 7 exposed at the lateral side of the syringe.

Figure 4B:
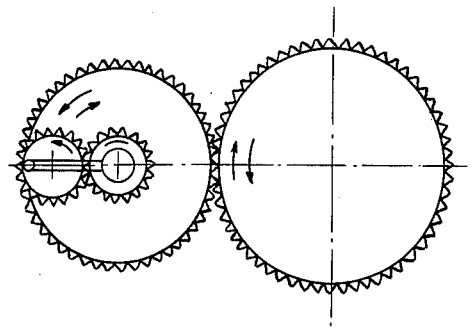
FIG. 4b is a section taken through FIG. 4 showing a modification in which gearwheels are used in place of rubber rollers.

Referring to FIGS. 3 and 4b, the housing is provided interally with a bearing 17 in which is journalled a driven shaft 16 adapted to couple with the output shaft of the drive unit 11. The shaft 16 is fast with a pinion 19 meshing with a pinion 20 having a shaft 24 journalled in the bearing so as to be parallel to shaft 16. The pinion 17 has an eccentric crank pin 21, the shape of which is immaterial but which preferably, has a curved profile. Arranged on the shaft 16 so as to rotate freely with respect thereto, is a gear 23 which meshes with the serrated thumb-wheel 7 when the device 20 is mounted on the syringe. The gear 23 has a groove 22 in which engages the crank-pin 21 whereby, as indicated in FIG. 4b, continuous rotation of the pinion 20 is converted into oscillation of the gear 23 about the shaft 16, and hence oscillation of the thumb-wheel 7 and sleeve 6 about their common axis.

Figure 4A:
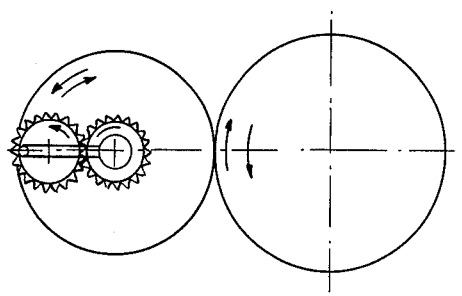
FIG. 4a is a section through FIG. 4.
Figure 4:
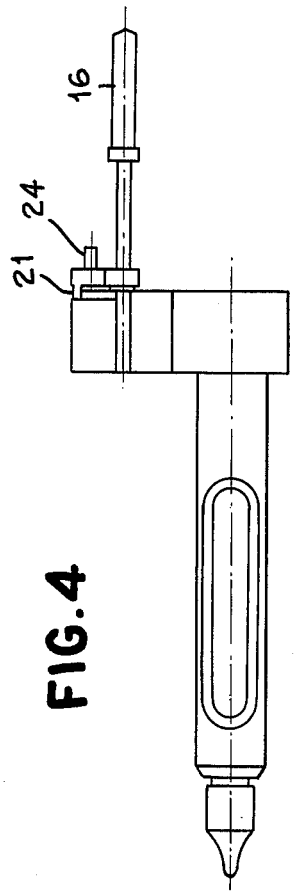
FIG. 4 is a view looking in the same direction as FIG. 2, showing certain of the parts of the syringe and oscillating device.

In modification as shown in FIGS. 4 and 4a, the syringe is provided with a thumb-wheel in the form of a rubber roller, and the gear 23 of the device 10 is replaced by a grooved rubber roller in frictional engagement with the thumb-wheel.

Figure 5A:
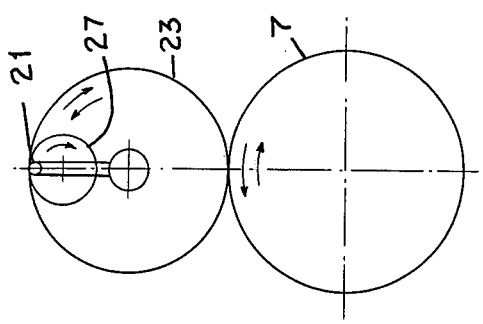
FIG. 5a is a section taken through FIG. 5.
Figure 5:
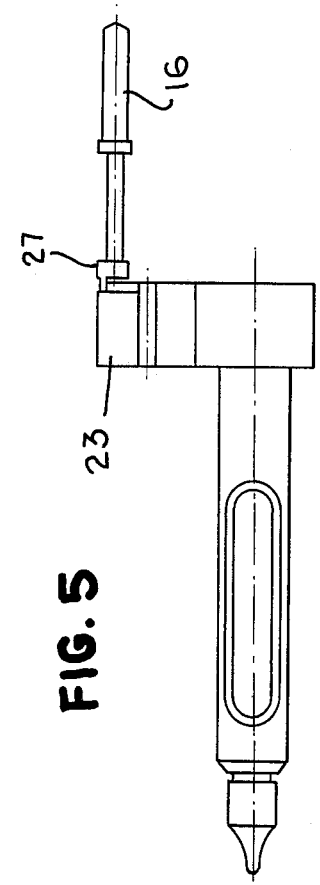
FIG. 5 is a view similar to FIG. 4 but of a further modification.

In the embodiment shown in FIGS. 5 and 5a, the driven shaft 16 is arranged offset relative to the axis of the toothed gear or rubber roller 23. The shaft 16 has a plate or crank 27 with a crank pin engaging in a groove in the roller, whereby oscillation of the wheel 23 and thumb-wheel 7 is produced as before.

Figure 6A:
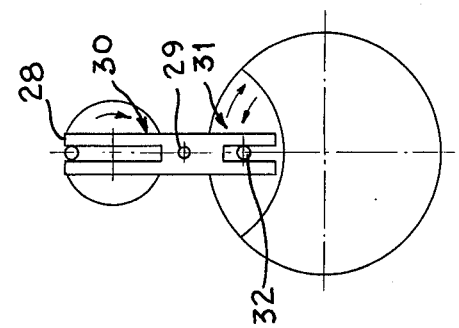
FIG. 6a is a section taken through FIG. 6.
Figure 7:
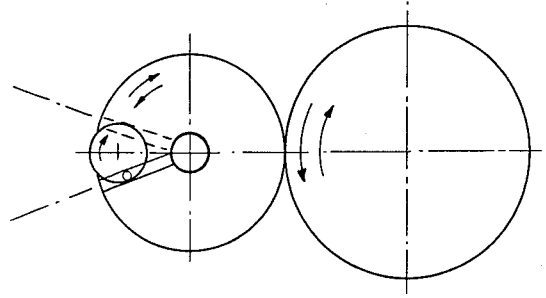
FIG. 7 is a view showing an intermediate position of the arrangement shown in FIG. 6.
Figure 6:
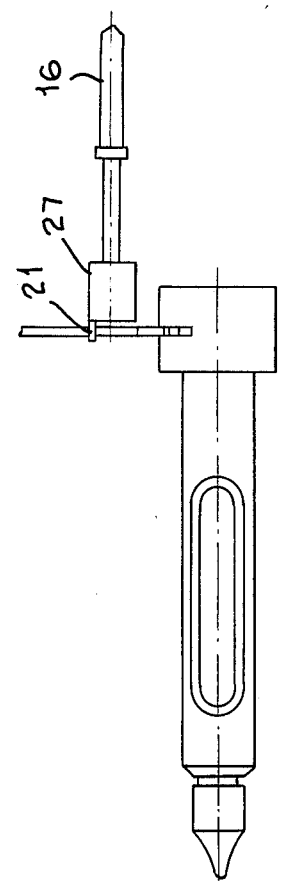
FIG. 6 is a view similar to FIG. 4 but of a further modification.

In the embodiment shown in FIGS. 6, 6a and 7, the driven shaft 16 is provided at its end with a crank or plate 27 having the crank pin 21. A fixed spindle 29 is arranged between the driven shaft 16 and the thumb wheel 7 and supports a member 30 having bifurcated ends 28 and 31. The crank pin 21 engages the bifurcated end 28 while a stud 32 on the thumb-wheel engages the bifurcated end 31. Rotation of the shaft 16 causes the member 30 to oscillate about its spindle and to trasmit this oscillation to the thumb-wheel and sleeve 6.

Although specific arrangements have been disclosed for causing the needle 8 to oscillate about its axis, it will be apparent to those skilled in the art that other mechanisms well known for translating rotary motion to oscillating motion may be used for the same purpose. Further, any such mechanism may be built-in to a syringe during manufacture, so that it is necessary in use to do no more than couple the purpose-constructed syringe to the drive head. Alternatively, the drive mechanism might be incorporated into the syringe and be made to begin to operate when the handle is initially squeezed. It is intended that all such mechanisms and alternatives are within the spirit and scope of the invention.

I claim:

1. In a syringe for injecting an anaesthetic or other liquid comprising a container for such liquid, a needle, and handle means responsive to pressure of the handle to cause liquid to be ejected from the needle and a manually rotatable wheel for rotating said needle, the improvement comprising power means for driving said wheel in oscillating back and forth rotation so as to effect back and forth oscillation of the needle about its axis during the injection operation.

2. A syringe according to claim 1, wherein said power means comprises transmission means integral with or attached to the syringe for translating continuous rotation of a drive unit known in dentistry into oscillatory motion of the said wheel.

3. A syringe according to claim 2, wherein said power means comprises a housing, a driven shaft mounted for rotation in said housing, coupling means coupling said driven shaft to said drive unit, said driven shaft being provided with a first pinion, a second pinion in mesh with said first pinion, a crank pin extending from said second pinion eccentric with respect thereto, a wheel freely rotatable about the axis of said driven shaft, said wheel having a groove in which said crank pin is positioned, said wheel being drivingly engaged with said manually rotatable wheel.

4. A syringe according to claim 2, wherein said power means comprises a housing, a driven shaft mounted for rotation in said housing, means coupling said driven shaft to said drive unit, said driven shaft being provided with an eccentric crank pin, a wheel freely rotatable about an axis parallel to said driven shaft, said wheel having a groove in which said crank is engaged, said wheel being drivingly engaged with said manually rotatable wheel.

5. A syringe according to claim 2, wherein said power means comprises a housing, a driven shaft mounted for rotation in said drive unit, said driven shaft being provided with an eccentric crank pin, said manually rotatable wheel having an eccentric stud, and a pivotal two armed lever, one arm of said lever engaging the crank pin and the other arm engaging the stud.

* * * * *